United States Patent
Breen et al.

(10) Patent No.: US 7,321,072 B2
(45) Date of Patent: Jan. 22, 2008

(54) PROCESS FOR PRODUCING PARAXYLENE BY METHYLATING TOLUENE WITH METHANOL AT A LOW CONTACTING TIME

(75) Inventors: John Paul Breen, Belfast (GB); Robert Burch, Antrim (GB); Paul John Collier, Reading (GB); Stanislaw Edmund Golunski, Reading (GB)

(73) Assignee: Johnson Matthey PLC, London (GB)

( * ) Notice: Subject to any disclaimer, the term of this patent is extended or adjusted under 35 U.S.C. 154(b) by 43 days.

(21) Appl. No.: 10/545,770

(22) PCT Filed: Feb. 18, 2004

(86) PCT No.: PCT/GB2004/000648

§ 371 (c)(1), (2), (4) Date: Jun. 15, 2006

(87) PCT Pub. No.: WO2004/074219

PCT Pub. Date: Sep. 2, 2004

(65) Prior Publication Data

US 2006/0264685 A1    Nov. 23, 2006

(30) Foreign Application Priority Data

Feb. 18, 2003   (GB) ................................ 0303659.7

(51) Int. Cl.
*C07C 2/66*   (2006.01)

(52) U.S. Cl. .................................................... 585/467
(58) Field of Classification Search ................ 585/467
See application file for complete search history.

(56) References Cited

U.S. PATENT DOCUMENTS

| | | | |
|---|---|---|---|
| 3,965,208 A | 6/1976 | Butter et al. | |
| 4,067,920 A | 1/1978 | Kaeding | |
| 4,152,364 A | 5/1979 | Chu | |
| 4,158,024 A | 6/1979 | Kaeding et al. | |
| 4,250,345 A | 2/1981 | Chu | |
| 4,377,718 A | 3/1983 | Sato et al. | |
| 5,939,597 A | 8/1999 | Dessau et al. | |

FOREIGN PATENT DOCUMENTS

| | | |
|---|---|---|
| JP | 54-144324 | 11/1979 |
| JP | 56045419 A | 4/1981 |
| JP | 58035130 A | 3/1983 |
| WO | WO-98/14415 | 4/1998 |

OTHER PUBLICATIONS

Kaeding et al., "Selective Alkylation of Toluene with Methanol to Produce *para*-Xylene," *Journal of Catalysis*, vol. 67, 1981, pp. 159-174.

Minachev et al., "Space Surface Characteristics and Catalytic Properties of Pentasil Systems in Reaction of Toluene with Methanol in Dependence of Their Composition, Modification Manner and Thermotreatment Conditions," Proc. 9th Int. Congress of Catalysis, 1988, pp. 461-467.

Xie et al., "Dispersion of Oxides on HZSM-5 and Threshold Effect on Shape-Selective methylation of Toulene," ACS Symposium Series No. 738, Shape Selective Catalysis, 2000, pp. 188-200.

*Primary Examiner*—Thuan Dinh Dang
(74) *Attorney, Agent, or Firm*—RatnerPrestia

(57) ABSTRACT

A process for producing para-xylene by the selective methylation of toluene comprising contacting a reactant mixture comprising toluene, methanol and added water, with an oxide modified ZSM-5 zeolite catalyst in a flow reactor in conditions selected to limit coke formation on the catalyst and at a contact time, between reactant mixture and catalyst, of less than 1 second.

19 Claims, 4 Drawing Sheets

PROCESS FOR PRODUCING PARAXYLENE BY METHYLATING TOLUENE WITH METHANOL AT A LOW CONTACTING TIME

This application is the U.S. national phase application of PCT International Application No. PCT/GB2004/000648, filed Feb. 18, 2004, and claims priority of British Patent Application No. 0303659.7, filed Feb. 18, 2003.

FEILD OF THE INVENTION

This invention relates to an improved process for the selective methylation of toluene to para-xylene.

BACKGROUND OF THE INVENTION

Para-xylene is a key intermediate in the synthesis of tetraphthalic acid. When methanol and toluene are passed over a heated bed of ZSM-5 zeolite, an equilibrium mixture of xylene isomers is formed. At temperatures of between 350 and 650° C., the equilibrium mixture is approximately 23% para-xylene, 51% meta-xylene and 26% ortho-xylene (W W Kaeding et al., Jn. of Catalysis, Vol. 67, 1981, pp 159-174). The selectivity to para-xylene can be enhanced by modifying the external and internal surfaces of the zeolite with oxides (K M Minachev et al., Proc. $9^{th}$ Int. Congress of Catalysis, 1988, pp. 461-467).

U.S. Pat. No. 3,965,208 discloses an additional method for improving selectivity to para-xylene. A high temperature process (550-600° C.) is used at high space velocities. This reduces the contact time of the reactants with the catalyst. At such temperatures the catalyst becomes 'coked'. This is beneficial as it has the effect of blocking external acid sites on the catalyst thus preventing isomerisation of the para-xylene. Selectivity is thus improved. However, 'coking' of the catalyst reduces the overall conversion of reactants to products. U.S. Pat. No. 3,965,208 teaches that increasing the reaction temperature improves the overall conversion efficiency, whereas lowering the temperature reduces conversion. The catalyst has to be periodically regenerated, or 'de-coked' to maintain an adequate balance between selectivity and conversion with a practicable process temperature. Under these conditions, increasing space velocity, or reducing contact time, is beneficial.

Another process for producing para-xylene by methylation of toluene is described in Japanese Laid-Open Patent Publication No. 144,324/1979, wherein a crystalline aluminosilicate catalyst is used and improving selectivity is observed at shorter contact times (see FIG. 2b). The document reports that whilst it is possible to increase the toluene conversion by prolonging the contact time, this reduces the para-xylene selectivity.

WO 98/14415 describes a process for the catalytic selective production of para-xylene using a catalyst derived from an optionally oxide modified ZSM-5. The catalyst is obtained by contacting the ZSM-5 with steam at temperatures of at least 950° C. The process is conducted at a temperature of from 500 to 700° C. and preferably from 500 to 600° C. pressures of from 100 KPa to 7000 KPa and a typical methanol utilisation of 50-70% wherein the catalyst accumulates coke as it catalyses the toluene and methylation reaction.

In addition to the toluene and methanol, WO 98/14415 contemplates adding hydrogen and/or water to the reaction mixture. It is clear from this that hydrogen and/or water is included in an effort to control excessive coke formation on the catalyst to extend the period between catalyst regenerations and/or to maintain conversion within acceptable limits We have now discovered, very surprisingly, that by adding water to the reactant mixture and by reducing the contact time of the reaction mixture with the catalyst to below one second, it is possible to obtain industrially useful para-xylene selectivity with oxide modified ZSM-5 catalysts in conditions, such as temperature, wherein coking is limited or avoided.

DETAILED DESCRIPTION OF THE INVENTION

According to one aspect, the invention provides a process for producing para-xylene by the selective methylation of toluene, the process comprising contacting a reactant mixture comprosing toluene, methanol and added water, with an oxide modified ZSM-5 zeolite catalyst in a flow reactor in conditions selected to limit coke formation on the catalyst and at a contact time, between reactant mixture and catalyst, of less than 1 second.

It will be appreciated that for every mole of methanol that reacts with toluene in the system, one mole of water will result. For the avoidance of doubt, by added water herein we mean: "in excess of the amount produced in situ."

Without wishing to be bound by any theory, we believe that the added water in the present invention serves to promote para-xylene selectivity for at least two reasons. Firstly, it suppresses or reduces dehydration of the methanol e.g. $2CH_3OH \rightarrow C_2H_4 + 2H_2O$; and $2CH_3OH \rightarrow CH_3OCH_3 + H_2O$ and other undesirable side reactions which can lead to coke formation. Secondly, it acts as a diluent for controlling contact time.

The process of the invention indicates that the rate of toluene methylation within a ZSM-5 zeolite, and the rate of para-xylene diffusion through a modified channel structure, are both sufficiently high to allow high throughputs of reactant molecules to be used, without the conversion of toluene to para-xylene being sacrificed. In fact, it is possible to obtain selective methylation of toluene at levels greater than 90%. The key benefit of operating at a low contact time is that it suppresses the re-isomerisation of para-xylene molecules as they emerge from the channels and come into contact with the external surfaces of the ZSM-5 zeolite. The ability to change catalytic performance by changing operating conditions makes the design of the catalyst much less critical.

Suitably, the added water is present in the range of from 1 mole of water per mole of methanol to 70 moles of water per mole of methanol in the reactant mixture. In one embodiment, the added water is present in the range of from 4 to 12 moles of water per mole of methanol.

Preferably, the contact time of the reactant mixture with the catalyst is less than 0.6 seconds, more preferably, less than 0.3 seconds.

Lower contact times can be achieved for example, by using high reactant feed rates, a small catalyst bed size, the use of foam-like catalyst supports, or by adding a diluent to the reactants. The process may be carried out in fixed, moving or fluid catalyst beds, either individually or connected to form multiple bed catalytic reactors. Optionally, in a multiple bed arrangement, additional methanol can be introduced into the reaction mixture between beds to improve conversion.

The contact time is calculated by dividing the active catalyst volume by the reactant feed rate at normal temperature and pressure, i.e. 25° C. and 1 atmosphere pressure. In the instance where the catalyst is in particulate form, the active catalyst volume may be measured for example, by placing a known weight of catalyst in a graduated vessel and allowing the particles to settle into their natural packing density. The reactant feed rate is for example, measured by using calibrated syringe pumps or mass flow controllers. The sum of all reactants, including any carrier gas, is used to determine the reactant feed rate. A worked example calculation is shown below:

Reactant Feed Rate

| Methanol vapour: | 1.85 cm$^3$min$^{-1}$ |
| Toluene vapour: | 14.8 cm$^3$min$^{-1}$ |
| Steam: | 16.65 cm$^3$min$^{-1}$ |
| Hydrogen: | 99.9 cm$^3$min$^{-1}$ |
| Total: | 133.2 cm$^3$min$^{-1}$ or 2.22 cm$^3$s$^{-1}$ |

Active Catalyst Volume 0.3 g of catalyst particles were allowed to settle to their natural packing density in a graduated measuring cylinder. The particles occupied a volume of 0.6 cm$^3$.

Contact Time $$\text{Contact time} = \text{active catalst volume/reactant feed rate}$$
$$= 0.6 \text{ cm}^3 / 2.22 \text{ cm}^3\text{s}^{-1}$$
$$= 0.27 \text{ s}$$

Other methods of measuring the active catalyst volume will be known to those skilled in the art as will other techniques for determining the reactant feed rate. For example, if the catalyst is in the form of a coated substrate, the active catalyst volume is equivalent to the volume of the catalyst applied in the coating.

The prior art (e.g. U.S. Pat. No. 4,152,364) teaches that toluene can be methylated to para-xylene at weight hourly space velocities between 1 and 2000. However, the process is usually exemplified and studied at WHSV between 1 and 12 (see U.S. Pat. Nos. 4,067,920, 4,152,364, 4,158,024, 4,250,345 and 5,939,597). In Example 2 of U.S. Pat. No. 4,152,364, a 4/1 molar mixture of toluene/methanol is fed at a WHSV of 10 to a catalyst bed containing 5 g of modified zeolite. This means that the actual feed rate of the mixture is 50 g per hour, and the molar feed rate is 0.5 mol per hour of toluene and 0.125 mol per hour of methanol. Expressed as a flow of gas at normal temperature and pressure, the total feed rate is 4.2 cm$^3$ per second. Assuming that the natural packing density of the modified zeolite is 0.5 g per cm$^3$, the contact time is 2.38 s. The range of 1-2000 claimed for the WHSV, therefore corresponds to contact times between 23.8 s and 0.012 s.

The process of the present invention is carried out in conditions, such as temperature, selected to limit coke formation on the catalyst. A suitable combination of condition parameters whereby this is achieved can be determined empirically by the person skilled in the art. Indicators for catalyst coking include:

(i) catalyst discolouration;
(ii) relatively low methanol selectivity to para-xylene e.g. <70% such as <60% or <50%. "Methanol selectivity to para-xylene" herein, is also referred to as "methanol utilisation" in the prior art; and
(iii) toluene conversion failing off.

Conditions that limit coke formation include the nature of the catalyst; relatively lower temperatures; higher toluene methanol ratios in the reactant mixture; increased pressure; and increased diluent in the reaction mixture.

In the process of the invention, the preferred mole ratio of toluene to methanol in the reactant mixture is between 1 and 10, and in one embodiment, between 4 and 10 (See Example 8).

The process of the invention produces high degrees of conversion. When expressed as a percentage of the amount (in moles) of methanol supplied, a degree of conversion in excess of 75% is commonly achieved, and in certain cases substantially complete conversion (100%) is achieved. Degree of conversion, when expressed as a percentage of the amount of toluene supplied may be numerically lower, however this is a consequence of the ratio of toluene to methanol in the reactant mixture. For example, a degree of conversion of 12.5% in terms of toluene supplied in a reactant mixture where the ratio of toluene to methanol is equal to 8, corresponds to a 100% (12.5×8) conversion in terms of methanol supplied.

The process also demonstrates high selectivity to para-xylene. Preferably, the product mixture comprises in excess of 85% para-xylene, more preferably, in excess of 90% expressed with respect to the degree of conversion. With reference to the aforementioned example, the product mixture will comprise an excess of unconverted toluene, due to its 8 fold excess with respect to methanol in the original reactant mixture however, of the converted reactants, the major product will be para-xylene, with only small amounts of other xylene isomers and other products.

The reactant mixture may comprise hydrogen. Some hydrogen will invariably be present under process operating conditions with both known processes and the present process, however, during tests, the applicants found that increasing the hydrogen concentration improved selectivity. The precise reasons for this are not clear although it is suspected that a certain threshold amount of hydrogen benefits the process by suppressing unwanted side reactions. Equally or additionally, hydrogen may simply act as a diluent and similar benefits could be achieved by using nitrogen or other inert gases.

Preferably, the catalyst comprises an oxide modified ZSM-5 zeolite comprising boron, magnesium, calcium, lanthanum, phosphorus and antimony and mixtures of any two or more thereof. B$_2$O$_3$ modified ZSM-5 zeolites have been found to be particularly suitable, although other oxide modified ZSM-5 zeolites may be equally suitable, and will be known to those skilled in the art. Suitably, the oxide modifier is present in a weight percentage of from 5-15 wt %, with respect to the overall catalyst weight.

The invention will now be described by way of example only and with reference to the following drawings in which:

EXAMPLE 1

Figure 1:
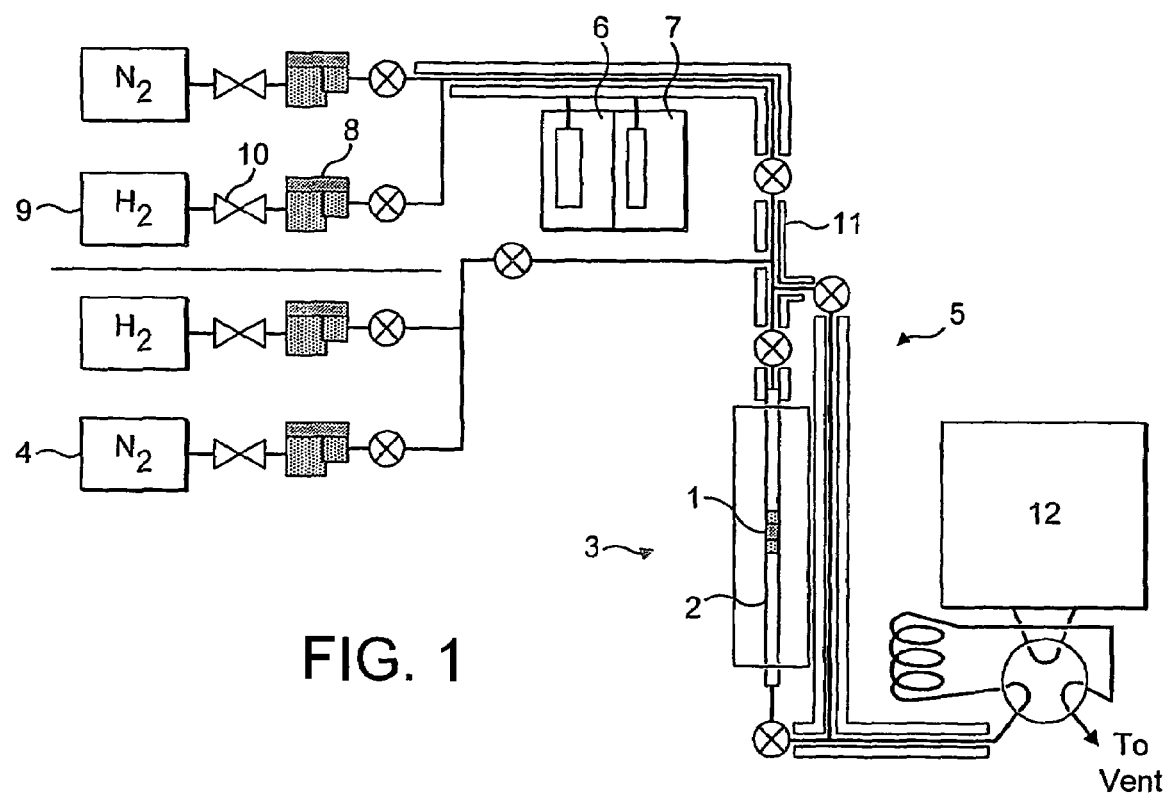
FIG. 1 is a schematic diagram of a reactor suitable for demonstrating the process of the present invention.

Comparative Example not According to the Invention of an Unmodified ZSM-5 Zeolite at Low Contact Time A commercially manufactured sample of HZSM-5 with a silica/alumina ratio of 80 was pressed into discs, which were then crushed and sieved to produce particles in the size range 250 μm-850 μm. A packed bed of catalyst was prepared by mixing 0.3 g of the particles with 0.7 g of powdered cordierite (a catalytically inert filler), and loading the mixture midway along the length of a quartz tube reactor while it was held vertically. The bed was held in place by plugs of quartz wool. The reactor was mounted horizontally inside a tube furnace, so that the catalyst bed was both at the radial and axial centre of the furnace.

A flow of 50 $cm^3$ $min^{-1}$ of nitrogen was passed through the catalyst bed for 30 minutes while the furnace temperature was ramped to 440° C. After the 30 minutes had elapsed, the flow was switched so that it bypassed the reactor, and left the catalyst bed isolated in an atmosphere of static nitrogen. Syringe pumps, supplying the liquid feeds (methanol, toluene and water), and a mass-flow controller, supplying hydrogen, were turned on. The liquid and gas flows were heated to 180° C. to produce a homogeneous gas-phase mixture (the reactant feed), which comprised methanol vapour (1.85 $cm^3$ $min^{-1}$), toluene vapour (14.8 $cm^3$ $min^{-1}$), steam (16.65 $cm^3$ $min^{-1}$), and hydrogen (99.9 $cm^3$ $min^{-1}$). After 30 minutes, the reactant feed was fed to the reactor. As the volume of active catalyst was 0.6 $cm^3$ and the reactant feed rate was 2.2 $cm^3$ $s^{-1}$, the contact time was 0.27 s.

The exit-stream from the reactor was analysed by gas chromatography. As shown in Table 1, the product stream, which had stabilised after 15 minutes, contained a near equilibrium concentration of para-xylene and sub-equilibrium concentrations of the ortho and meta isomers. The other products formed were benzene and $C_9$ aromatics. The latter were formed by disproportionation of some of the toluene, explaining why the toluene conversion was higher than expected for toluene methylation alone.

EXAMPLE 2

10% Mg/ZSM-5 at Low Contact Time

A commercially manufactured sample of HZSM-5 with a silica/alumina ratio of 80/1 was modified by impregnation with an aqueous solution of magnesium nitrate. The amount of impregnating solution added was calculated to result in a magnesium loading of 10% by weight. The impregnated ZSM-5 zeolite was dried (120° C., 16 h, air) and calcined (500° C., 2 h, air).

The modified ZSM-5 zeolite was tested in exactly the same way as described in Example 1. As shown in Table 1, the conversion of toluene was lower than for the unmodified ZSM-5 zeolite, with the major product being para-xylene. Apart from small amounts of ortho- and meta-xylene, no other products were detected. The performance showed that the toluene was being methylated to para-xylene with greater than 95% selectivity.

EXAMPLE 3

10% Mg/ZSM-5 Over Range of Contact Times

A sample of 10% Mg/ZSM-5, prepared by the method described in Example 2, was pressed into discs, which were then crushed and sieved to produce particles in the size range 250 μm-850 μm. A packed bed of catalyst was prepared by mixing 0.3 g of the particles with 0.7 g of powdered cordierite, and loading the mixture midway along the length of a quartz tube reactor, as described in Example 1.

A flow of 50 $cm^3$ $min^{-1}$ of nitrogen was passed through the catalyst for 30 minutes while the furnace temperature was ramped to 440° C. After the 30 minutes had elapsed, the flow was switched so that it bypassed the reactor, and left the catalyst isolated in an atmosphere of static nitrogen. Syringe pumps, supplying methanol, toluene and water, and a mass-flow controller supplying hydrogen were turned on. The liquid and gas flows were heated to 180° C. to produce a homogeneous gas-phase mixture (the reactant feed), which comprised methanol vapour (0.4 $cm^3$ $min^{-1}$), toluene vapour (3.2 $cm^3$ $min^{-1}$), steam (3.6 $cm^3$ $min^{-1}$), and hydrogen (7.2 $cm^3$ $min^{-1}$). After 30 minutes, the reactant feed was fed to the reactor at 440° C. The contact time between the reactant feed and the catalyst bed was 2.54 seconds.

Figure 2A:
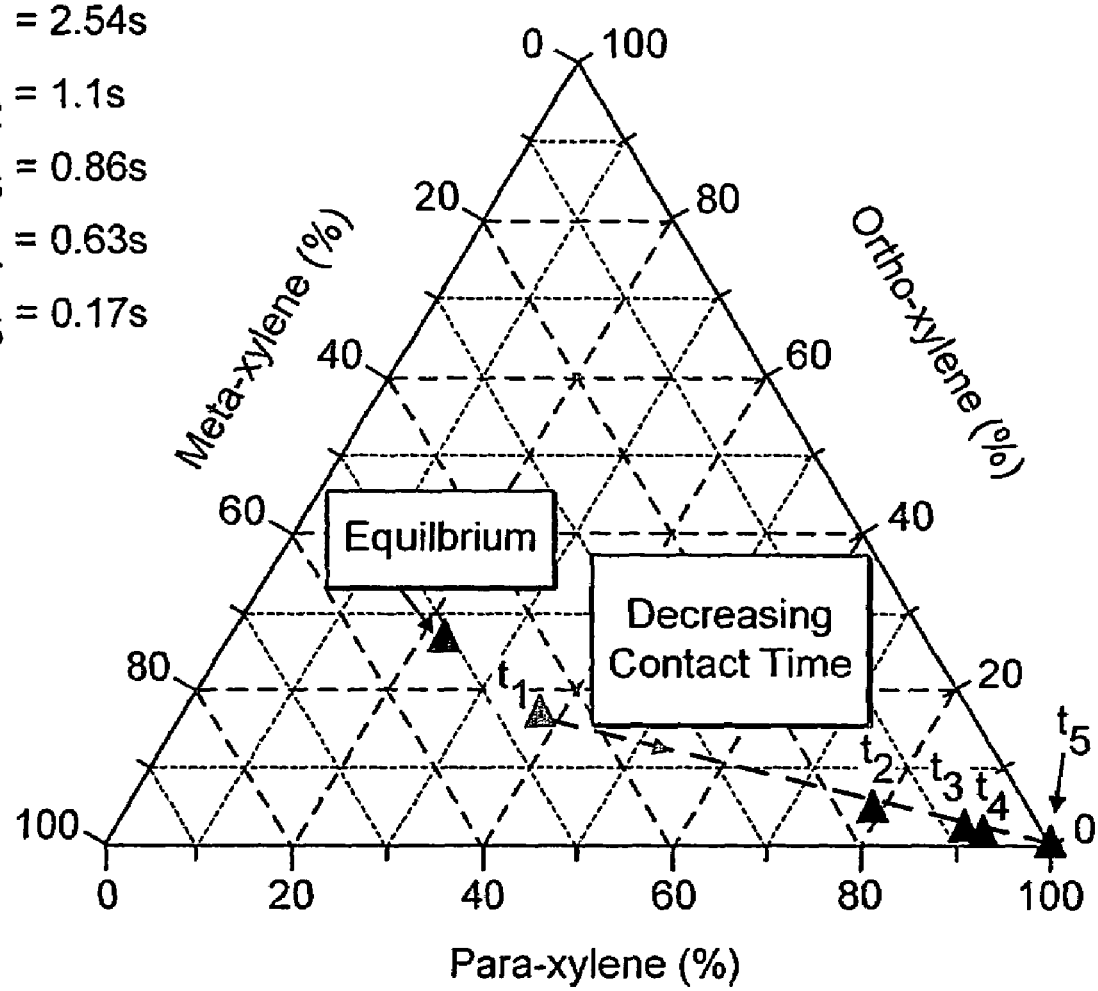
FIG. 2a is a graph showing the effect of lowering the contact time by adding a diluent to the reactant feed, including added water, at 440° C. for an example of a process according to the present invention.

After 15 minutes on line, the catalyst reached a stable level of performance. The conversion was close to the expected maximum for toluene methylation (12.5%), while the selectivity to para-xylene was about 40%. The contact time between the reactant feed and the catalyst bed was then lowered in 5 steps, by increasing the hydrogen flow rate. The selectivity to para-xylene increased as the contact time was lowered (as shown in FIG. 2a), but the toluene conversion remained unchanged. The selectivity reached 100% when the hydrogen flow-rate was raised to 192.8 $cm^3$ $min^{-1}$ corresponding to a contact time of only 0.17 s at 440° C.

Figure 2B:
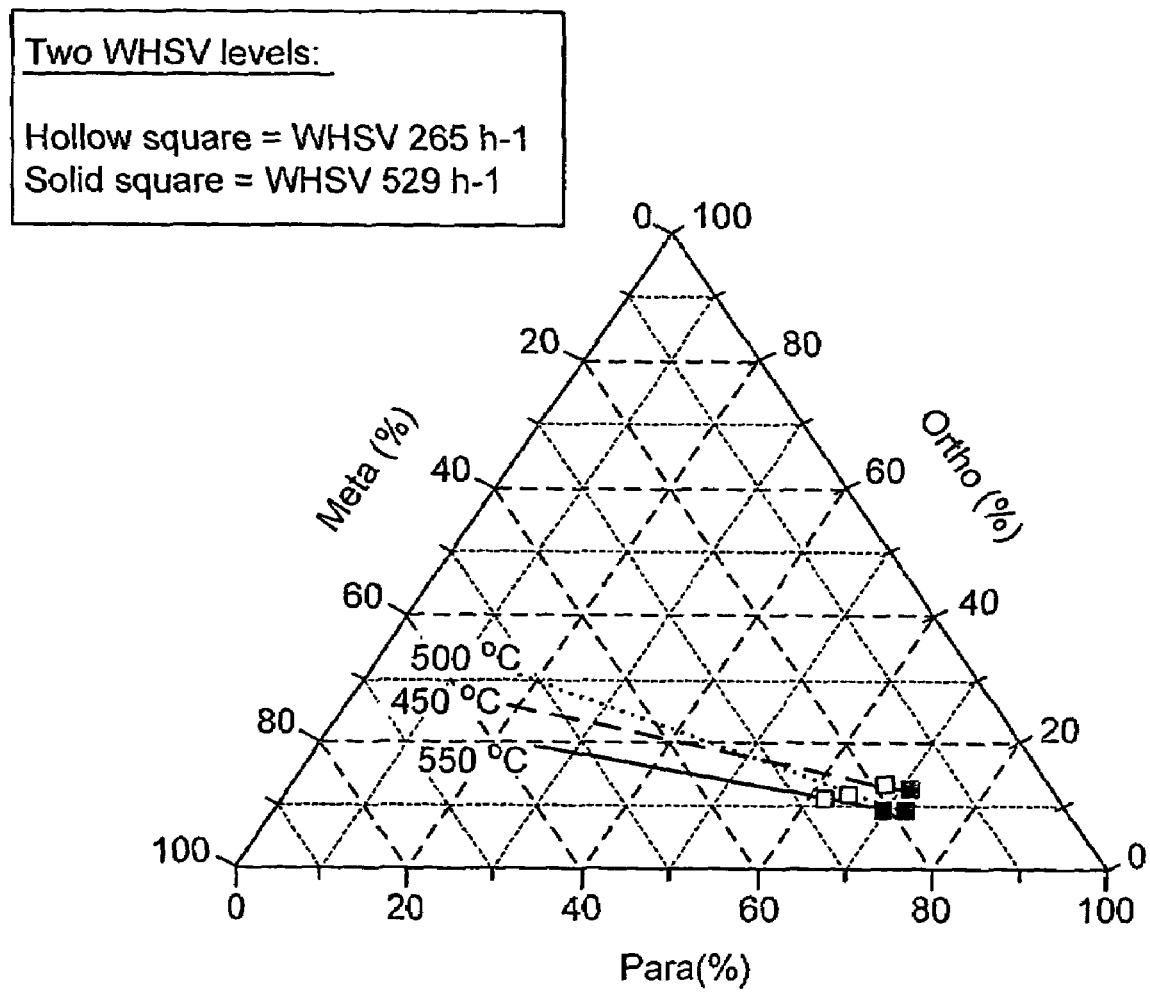
FIG. 2b is a graph showing the effect of lowering the contact time by increasing reactant feed rate at three different temperatures according to Japanese Laid-Open Patent Publication No. 144,324/1979; and, FIG. 3 is a graph showing the effect of lowering the contact time, by adding diluent, on the isomerisation of para-xylene.

Contrastingly, FIG. 2b shows a similar ternary plot based on the results from Japanese Laid-Open Patent Publication No. 144,324/1979. It can be seen that as the temperature is increased from 450° C. to 500° C. the improvement in para-xylene selectivity is more marked and we understand that this difference results from catalyst coking, as taught in U.S. Pat. No. 3,965,208. However, assuming that the contact time at WHSV 529 $h^{-1}$ is 0.74 s, it is clear that for a similar contact time of 0.63 s ($t_4$ in FIG. 2a) the process of the present invention achieves significantly better para-xylene selectivity at 440° C.

EXAMPLE 4

Para-Xylene Isomerisation by 10% Mg/ZSM-5

At the maximum hydrogen flow-rate reached in Example 3 (contact time 0.17 s), the toluene in the feed was replaced by para-xylene. The reactant feed now contained a concentration of para-xylene which was equivalent to that of the toluene it replaced. After 15 minutes, the exit-stream was analysed, and was found to contain para-xylene as the predominant (>95%) form of xylene. This showed that, once formed, the para isomer is not isomerised by 10% Mg/ZSM-5 at this low contact time.

Figure 3:
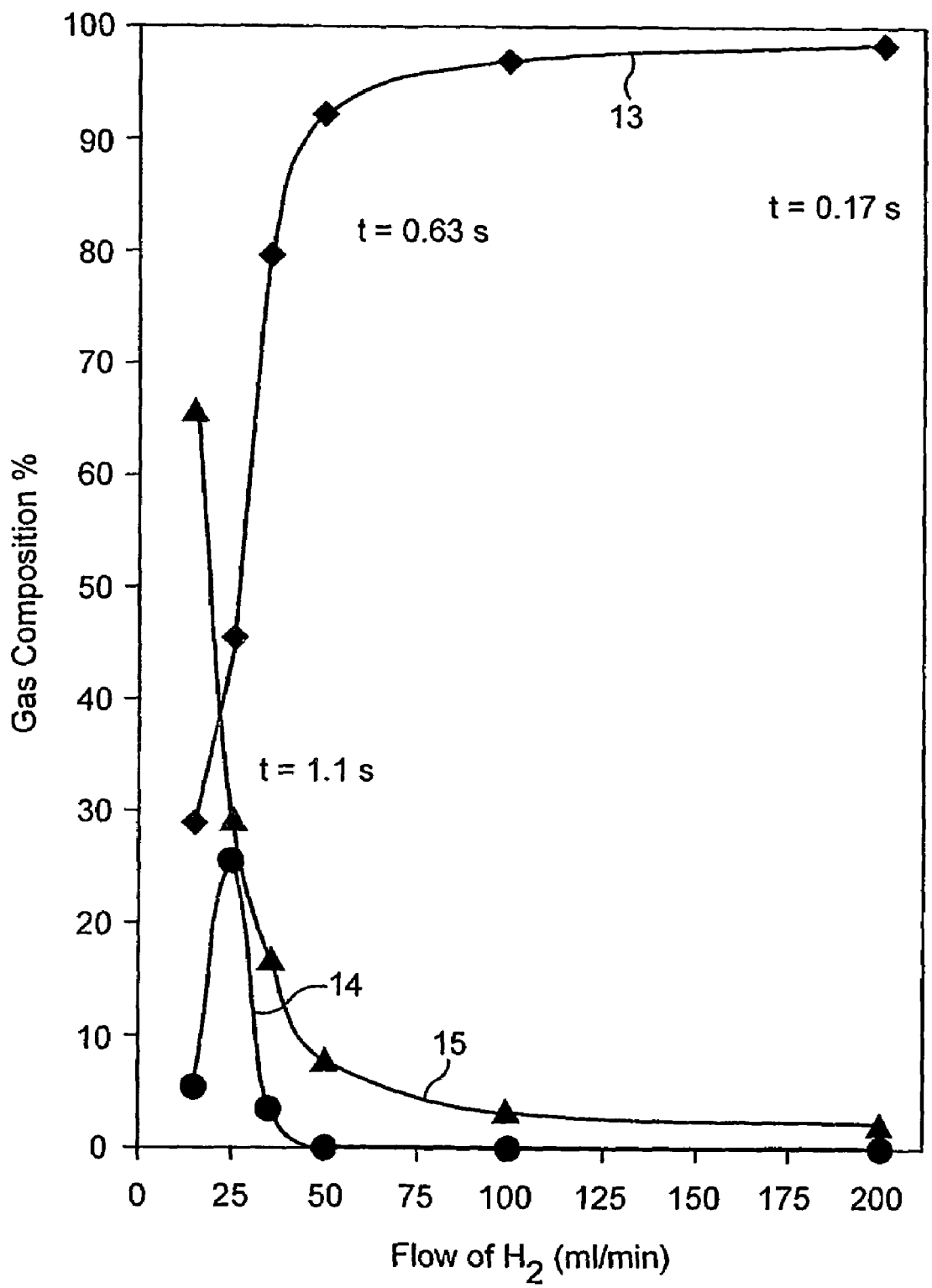

The contact time between the reactant feed and the catalyst was then increased in 5 steps, by decreasing the hydrogen flow rate. As shown in FIG. 3, the degree of isomerisation increased as a function of contact time. The most noticeable effect occurring at contact times above about 0.7 s.

When the results of Example 3 and Example 4 are considered together, they indicate that para-xylene can be selectively formed within the internal channel structure of 10% Mg/ZSM-5. At low contact times, as the para-xylene emerges, it is swept out of the catalyst bed before it can isomerise to ortho- and meta-xylene. At high contact times, the para-xylene can re-adsorb on sites on the external surfaces, where isomerisation can occur.

EXAMPLE 5

10% Mg/ZSM-5 Over Range of Contact Times in Absence of Hydrogen

The procedure described in Example 3 was repeated, except the hydrogen in the reactant feed was replaced by nitrogen. The catalyst showed the same performance trend as observed in Example 3. The selectivity to para-xylene was less than 40% at the lowest flow rate of nitrogen, and reached 99% at the highest flow rate. The results show that the presence of hydrogen is not essential to the catalyst achieving high selectivity.

EXAMPLE 6

10% Mg/ZSM-5 at High Liquid-Hourly Space Velocity

The procedure described in Example 2 was repeated, except the flow rate of hydrogen in the reactant feed was lowered to 66.6 $cm^3$ $min^{-1}$ prior to the reactor, which had the effect of increasing the contact time to 0.38 s. As shown in Table 1, when the catalyst performance stabilised, the conversion of toluene exceeded the value expected for complete methylation, indicating that some disproportionation was occurring. The selectivity to para-xylene was less than 90%.

After this test, the catalyst bed was removed and replaced by a mixture of 0.1 g 10% Mg/ZSM-5 and 0.9 g cordierite. The test procedure was then repeated, again using a hydrogen feed rate of 66.6 $cm^3$ $min^{-1}$ prior to the reactor. Under these conditions, the weight hourly space velocity of the toluene was 3× that in the previous test, and the contact time was therefore 0.13 s. The total liquid hourly space velocity (of methanol+toluene) was 42 $h^{-1}$, which was more than 8× that used by Minachev et al (Proc. $9^{th}$ Int. Congress of Catalysis, 1988, pp. 461-467) and 6× that used by Xie et al (ACS Symposium Series No 738, Shape Selective Catalysis, 2000, pp. 188-200) when testing Mg/ZSM-5. The conversion of toluene was now much closer to the value expected for methylation, and the selectivity to para-xylene exceeded 98%.

When considered together with the results from Examples 2-5, these data show the correlation between low contact time and high selectivity, both in terms of the desired reaction (toluene methylation) and in the formation of para-xylene. For a fixed bed size, low contact times can be achieved either by using a high weight-hourly space velocity of liquid feeds, or by adding a diluent (such as hydrogen or nitrogen) to the reactant feed.

EXAMPLE 7

10% B/ZSM-5 Over Range of Toluene/Methanol Ratios

A commercially manufactured sample of $NH_4ZSM-5$ with a silica/alumina ratio of 80/1 was dry milled with $B_2O_3$. The amount of $B_2O_3$ was calculated to result in a boron loading of 10% by weight. The milled mixture was calcined at 500° C. for 2 hours to form the 10% B/ZSM-5 catalyst.

A sample of 10% B/ZSM-5 was pressed into discs, which were then crushed and sieved to produce particles in the size range 250 µm-850 µm. A packed bed of catalyst was prepared by mixing 0.3 g of the particles with 0.7 g of powdered cordierite, and loading the mixture midway along the length of a quartz tube reactor, as described in Example 1.

A flow of 50-$cm^3$ $min^{-1}$ of nitrogen was passed through the catalyst for 30 minutes while the furnace temperature was ramped to 440° C. After the 30 minutes had elapsed, the flow was switched so that it bypassed the reactor, and left the catalyst isolated in an atmosphere of static nitrogen. Syringe pumps, supplying methanol, toluene and water, and a mass-flow controller supplying hydrogen were turned on. The liquid and gas flows were heated to 180° C. to produce a homogeneous gas-phase mixture (the reactant feed), which comprised methanol vapour (1.85 $cm^3$ $min^{-1}$), toluene vapour (14.8 $cm^3$ $min^{-1}$), steam (16.65 $cm^3$ $min^{-1}$), and hydrogen (66.6 $cm^3$ $min^{-1}$). After 30 minutes, the reactant feed was fed to the reactor at 440° C. Under these conditions, the toluene/methanol ratio in the feed was 8/1, and the contact time between the reactant feed and the catalyst was 0.36 s.

After 15 minutes on line, when the catalyst had reached a stable level of performance, the conversion matched the expected maximum for toluene methylation (12.5%), while the selectivity to para-xylene was 99.9%. The toluene/methanol ratio was then reduced in 2 steps to 4/1 and 1.3/1, by increasing the feed rate of methanol. As Table 1 shows, the conversion of toluene rose as more methanol was available for reaction. Although the conversion of methanol was close to 100% in each case, at the lower toluene/methanol ratios, some of the methanol was reacting with itself to form ethylene. However, the selectivity with which toluene was methylated to para-xylene remained high (94-100%).

EXAMPLE 8

10% B/ZSM-5 at High Liquid-Hourly Space Velocity

The procedure described in Example 7 was repeated, except the weight of 10% B/ZSM-5 in the catalyst bed was reduced to 0.1 g and the weight of cordierite increased to 0.9 g. Under these conditions, the weight hourly space velocity of the toluene was 3× that in the previous test, and the contact time was 0.12 s when the toluene/methanol ratio was 8/1. As Table 1 shows, the high selectivity of the catalyst was retained at the high weight hourly space velocity.

TABLE 1

Steady-state performance of modified ZSM-5 in comparison to unmodified HZSM-5 at 440° C.

| Catalyst | Example | WHSV | t | T/M | Conversion | Selectivity | | | |
|---|---|---|---|---|---|---|---|---|---|
| | | | | | | p-xylene | m-xylene | o-xylene | others |
| HZSM-5 | 1 | 11.12 h$^{-1}$ | 0.27 s | 8/1 | 22.6% | 24.7% | 40.5% | 22.0% | 12.9% |
| 10% Mg/ZSM-5 | 2 | 11.12 h$^{-1}$ | 0.25 s | 8/1 | 9.12% | 95.5% | 3.78% | 0.709% | 0% |
| 10% Mg/ZSM-5 | 6 | 11.12 h$^{-1}$ | 0.38 s | 8/1 | 16.2% | 87.5% | 8.48% | 2.48% | 1.56% |
| 10% Mg/ZSM-5 | 6 | 33.35 h$^{-1}$ | 0.13 s | 8/1 | 13.7% | 98.3% | 0.67% | 0% | 1.05% |
| 10% B/ZSM-5 | 7 | 11.12 h$^{-1}$ | 0.36 s | 8/1 | 12.5% | 99.9% | 0.08% | 0.03% | 0% |
| 10% B/ZSM-5 | 7 | 11.12 h$^{-1}$ | 0.35 s | 4/1 | 22.7% | 99.5% | 0.16% | 0.027% | 0.27% |
| 10% B/ZSM-5 | 7 | 11.12 h$^{-1}$ | 0.33 s | 1.3/1 | 32% | 94.6% | 1.22% | 0.58% | 3.63% |
| 10% B/ZSM-5 | 8 | 33.35 h$^{-1}$ | 0.12 s | 8/1 | 12.5% | 99.0% | 0.55% | 0.14% | 0.32% |
| 10% B/ZSM-5 | 8 | 33.35 h$^{-1}$ | 0.115 s | 4/1 | 24.1% | 98.3% | 0.63% | 0.18% | 0.86% |
| 10% B/ZSM-5 | 8 | 33.35 h$^{-1}$ | 0.11 s | 1.3/1 | 22.6% | 94.8% | 2.2% | 0.33% | 2.69% |

WHSV: weight-hourly space velocity of toluene
t: contact time between catalyst and reactant feed at normal temperature and pressure
T/M: molar toluene/methanol ratio
Conversion: mol toluene consumed × 100%/mol toluene supplied
Selectivity: mol % of products formed

The invention claimed is:

1. A process for producing para-xylene by the selective methylation of toluene, the process comprising contacting a reactant mixture comprising toluene, methanol and added water, with an oxide modified ZSM-5 zeolite catalyst in a flow reactor at a contact time, between reactant mixture and catalyst, of less than 1 second, wherein the process is carried out at a temperature of from 250 to 500° C.

2. The process according to claim 1, wherein the added water is present in the range of from 1 mole of water per mole of methanol to 70 moles of water per mole of methanol in the reactant mixture.

3. The process according to claim 1, wherein the added water is present in the range of from 4 moles of water per mole of methanol to 12 moles of water per mole of methanol.

4. The process according to claim 1, wherein the contact time of the reactant mixture with the catalyst is less than 0.6 seconds.

5. The process according to claim 1, wherein the contact time of the reactant mixture with the catalyst is less than 0.3 seconds.

6. The process according to claim 1, wherein the catalyst comprises a foam support.

7. The process according to claim 1, wherein the process is carried out at a temperature of from 300 to 500° C.

8. The process according to claim 1, wherein the oxide modifier is selected from the group consisting of boron, magnesium, calcium, lanthanum, phosphorus, antimony, and mixtures of any two or more thereof.

9. The process according to claim 8, wherein the oxide modifier is boron.

10. The process according to claim 8, wherein the oxide modifier is present in a weight percentage of 5-15% with respect to overall catalyst weight.

11. The process according claim 1, wherein the ratio of toluene to methanol in the reactant mixture is between 1 and 10.

12. The process according to claim 1, wherein a degree of conversion when expressed as a percentage of the amount of methanol supplied exceeds 75%.

13. The process according to claim 12, wherein a product mixture comprises in excess of 85% a para-xylene when expressed with respect to the degree of conversion.

14. The process according to claim 1, wherein the reactant mixture further comprises hydrogen.

15. The process according to claim 1, wherein the process is carried out at a temperature of from between 350 and 450° C.

16. The process according to claim 9, wherein the oxide modifier is present in a weight percentage of 5-15%, with respect to overall catalyst weight.

17. The process according to claim 1, wherein the ratio of toluene to methanol in the reactant mixture is between 4 and 10.

18. The process according to claim 12, wherein the product mixture comprises in excess of 90% para-xylene when expressed with respect to the degree of conversion.

19. The process according to claim 1, wherein the added water is present in the range of from 1 mole of water per mole of methanol to 5 moles of water per mole of carbon atoms in the reactant mixture.

* * * * *